US009154739B1

(12) United States Patent
Nicolaou et al.

(10) Patent No.: US 9,154,739 B1
(45) Date of Patent: Oct. 6, 2015

(54) PHYSICAL TRAINING ASSISTANT SYSTEM

(75) Inventors: Alex Nicolaou, Waterloo, CA (US);
Ryan James Harrison, Kitchener, CA (US)

(73) Assignee: Google Inc., Mountain View, CA (US)

( * ) Notice: Subject to any disclaimer, the term of this patent is extended or adjusted under 35 U.S.C. 154(b) by 980 days.

(21) Appl. No.: 13/307,143

(22) Filed: Nov. 30, 2011

(51) Int. Cl.
*H04N 7/18* (2006.01)
*A63B 26/00* (2006.01)
*G06K 9/00* (2006.01)

(52) U.S. Cl.
CPC .................................... *H04N 7/18* (2013.01)

(58) Field of Classification Search
CPC .. A61B 1/041; A61B 1/00036; A61B 1/0005; A61B 19/52; H04N 7/18
USPC ........................................................... 348/77
See application file for complete search history.

(56) References Cited

U.S. PATENT DOCUMENTS

| | | | | |
|---|---|---|---|---|
| 6,533,675 | B2 * | 3/2003 | Funk | 473/222 |
| 7,602,301 | B1 * | 10/2009 | Stirling et al. | 340/573.1 |
| 8,648,863 | B1 * | 2/2014 | Anderson et al. | 345/473 |
| 2002/0132703 | A1 * | 9/2002 | Martinez et al. | 482/8 |
| 2006/0247070 | A1 * | 11/2006 | Funk et al. | 473/222 |
| 2008/0094472 | A1 * | 4/2008 | Ayer et al. | 348/157 |
| 2008/0170123 | A1 * | 7/2008 | Albertson et al. | 348/157 |
| 2010/0022351 | A1 * | 1/2010 | Lanfermann et al. | 482/1 |
| 2010/0225765 | A1 * | 9/2010 | Kadogawa | 348/159 |
| 2012/0116719 | A1 * | 5/2012 | Takahashi et al. | 702/160 |
| 2012/0183939 | A1 * | 7/2012 | Aragones et al. | 434/247 |
| 2013/0190658 | A1 * | 7/2013 | Flaction et al. | 600/595 |
| 2014/0157209 | A1 * | 6/2014 | Dalai et al. | 715/863 |
| 2014/0228985 | A1 * | 8/2014 | Elliott et al. | 700/91 |
| 2015/0003687 | A1 * | 1/2015 | Utsunomiya et al. | 382/107 |

OTHER PUBLICATIONS

"Kinect," From Wikipedia, the free encyclopedia, http://en.wikipedia.org/wiki/Kinect, last modified on Nov. 20, 2011, accessed on Nov. 21, 2011, 19 pages.
"Your Shape: Fitness Evolved [Xbox 360 Game]," Google product search, http://www.google.com/products/catalog?h1=en&nord=1&q=your+shape+fitness+evolved&gs_upl=19533119533101197601111101010101158115810.11110&um=1&bav=on.2,or.r_gc.r_pw.r_cp.,cf.osb&ion=1&biw=1475&bih=806&ie=UTF-8&tbm=shop&cid=3588216318278668807&sa=X&ei=g6LJTsvhKKOUiQL1htnTDw&ved=0CFsQxBUwAA, accessed on Nov. 21, 2011, 4 pages.
"Machine Learning", http://en.wikipedia.org/wiki/Machine_learning, last modified Aug. 15, 2011, downloaded Aug. 24, 2011.

* cited by examiner

*Primary Examiner* — Sath V Perungavoor
*Assistant Examiner* — Howard D Brown, Jr.
(74) *Attorney, Agent, or Firm* — McDermott Will & Emery LLP

(57) ABSTRACT

A computer-implemented method, a system and a computer-readable medium provide useful feedback for a user involved in exercise. A camera is used to track user motion by using image processing techniques to identify key points on a user's body and track their motion. The tracked points are compared to proper form for an exercise, and an embodiment gives feedback based on the relationship between the actual movement of the user and the proper form. Alternatively, silhouette information may be used in a similar manner in another embodiment.

18 Claims, 8 Drawing Sheets

PHYSICAL TRAINING ASSISTANT SYSTEM

BACKGROUND

1. Field

Embodiments are generally related to providing useful feedback for a user involved in exercise.

2. Background

Correct form in resistance and other forms of physical training is essential for effectiveness and safety. After developing proper form under supervision, users regularly train on their own without having someone to actively correct them. Lack of supervision can lead to gradual changes in their execution and improper form. An approach that would be able to observe motion by a user and prompt with corrections in real time would help prevent or resolve this problem.

However, there is no current approach that can address the problem directly. One option would be to have another person watch a user periodically and correct the user's exercise form, but this requires another person to participate by observing and offering suggestions. Unfortunately, having another person provide suggestions requires finding another person. Furthermore, there is no guarantee that another person may be able to provide the right feedback, as another person may not be able to guarantee the accuracy of his or her observations or the usefulness or his or her suggestions.

Alternative approaches may use techniques that allow a user to observe himself or herself exercise. For example a user may use a video recording system and then review his or her own execution. However, using a video recording system lacks immediate, realtime feedback, making the feedback of less value. A mirror may provide immediate views to a user of his or her exercise, but a mirror is not useful for many activities and has a limited number of angles of viewing. Furthermore, approaches that rely on user judgement must deal with the problem that a user may not be able to identify problems with his or her own exercise form.

Hence, at present means of providing users with feedback about the correctness of their exercise form have serious deficiencies.

BRIEF SUMMARY

Useful feedback for a user involved in exercise is provided. In general, a camera acquires images of the user as he or she exercises. These images are processed to identify key points or silhouettes. By comparing the key points or silhouettes to key points or silhouettes for a proper form of the exercise, a system can determine if the exercise form is correct, or what suggestions to make to correct it.

In general, one innovative aspect of the subject matter described in this specification may be embodied in methods that include several actions. In one method embodiment, an indication is received of an exercise selection from a user. A body is detected in front of a camera. Key points are identified on the body based on the detecting. Motion is detected associated with the body and the key points are compared to a proper form while detecting the motion. A determination is made as to whether the comparison is within a predetermined range, and a response is provided to the user in response to the determination.

Other embodiments of these aspects include corresponding systems, apparatus, and computer programs, configured to perform the actions of the methods, encoded on computer storage devices.

In another innovative aspect of the subject matter described in this specification can include receiving a sequence of silhouettes of correct form associated with an exercise. Motion associated with the user is detected. A generic silhouette of a user at each of a predetermined number of times with a camera is recorded. The sequence of silhouettes is compared with the generic silhouette at each of the predetermined number of times. Feedback of the comparison is provided.

Other embodiments of these aspects include corresponding systems, apparatus, and computer programs, configured to perform the actions of the methods, encoded on computer storage devices.

Further embodiments, features, and advantages of the invention, as well as the structure and operation of the various embodiments of the invention are described in detail below with reference to accompanying drawings.

BRIEF DESCRIPTION OF THE FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

DETAILED DESCRIPTION OF EMBODIMENTS

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
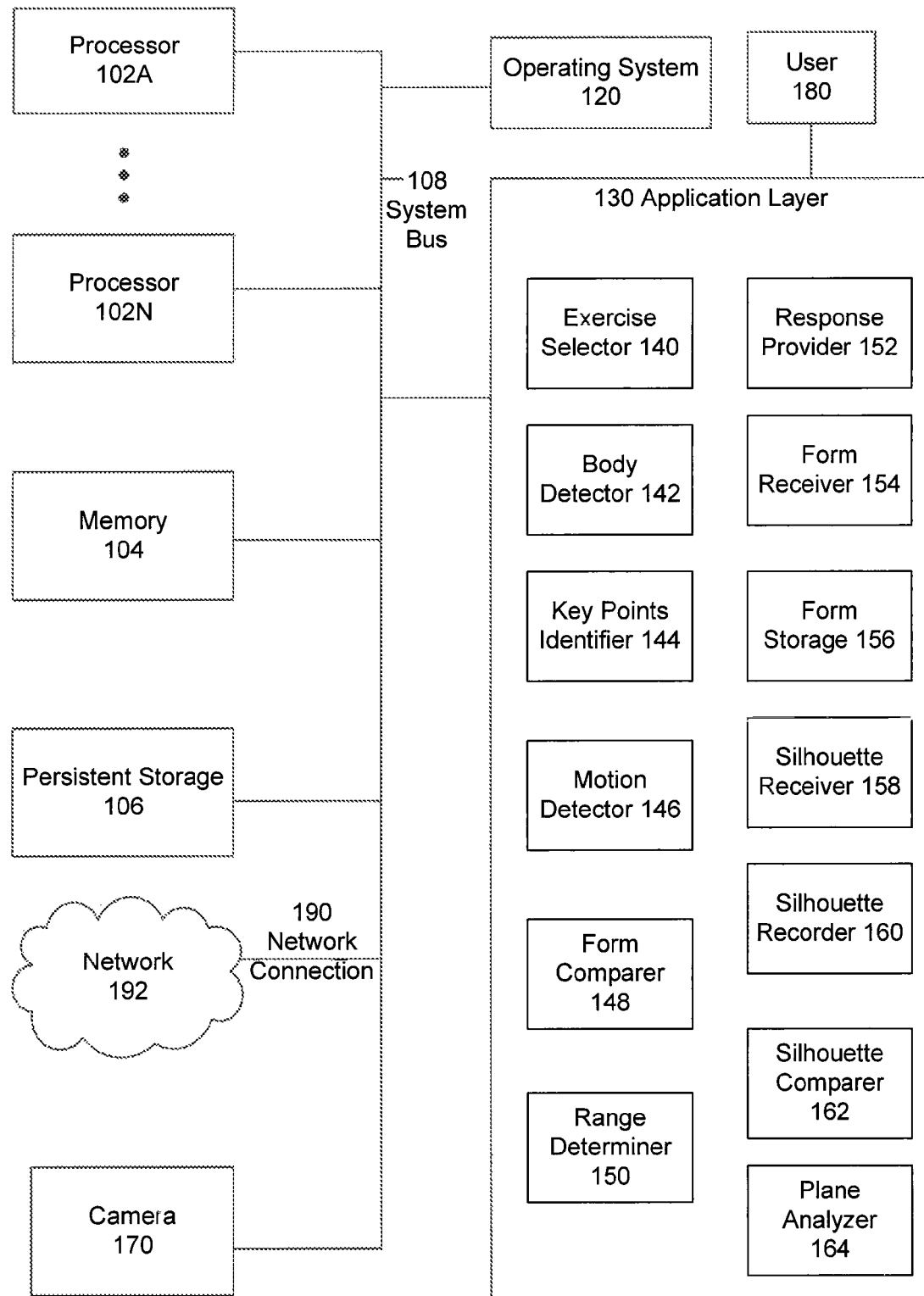
FIG. 1 is a diagram illustrating an exemplary system.

FIG. 1 is a diagram illustrating an exemplary system. Computer system 100 provides useful feedback for a user 180 involved in exercise.

Computer system 100 contains a combination of hardware, software, and firmware constituent parts that allow it to run an application layer 130 with access to additional resources over a network 192 via a network connection 190. Computer system 100 may be a conventional computer such as a desktop or laptop PC, but it may additionally be any web-enabled peripheral such as a game console, a tablet, a netbook or a smartphone. Computer system 100 as shown in FIG. 1 may be organized around a system bus 108, but any type of infrastructure that allows the hardware infrastructure elements of computer system 100 to communicate with and interact with each other may be used to function as this part of computer system 100.

Computer system 100 is coupled to a camera 170. In one embodiment, computer system 100 may be a mobile device such as a smartphone, laptop computer, netbook, or tablet computer, and computer system 100 may have a built-in camera 170. Built-in camera 170 may be, for example, an embedded front-facing or rear-facing camera. While computer system 100 may use multiple cameras, for example to obtain depth information, using only one camera 170 is sufficient.

Camera 170 can function without being embedded in a mobile device. For example, a desktop computer or a game console can be used as computer system 100, such that the desktop computer or game console is connected by a wired or wireless connection to camera 170. In these cases, camera 170 may be a webcam, a camera gaming peripheral, or a similar type of camera. However, it should be noted that a wide variety of computer system 100 and camera 170 implementations exist, and the examples presented herein are intended to be illustrative only.

The processing task in FIG. 1 is carried out by one or more processors 102A . . . 102N, but it should be noted that any type of processing technology may be used here, including multi-core processors, multiple processors, or distributed processors.

In order to manipulate data, processors 102A . . . 102N access a memory 104 via system bus 108. For data which needs to be stored more permanently, processors 102A . . . 102N access persistent storage 106. Processors 102A . . . 102N, memory 104 and persistent storage 106 operate in coordination with operating system 120 to provide basic functionality for computer system 100. Operating system 120 provides support functionality for application layer 130.

Application layer 130 includes several subsystems that cause computer system 100 to use its constituent parts to operate.

The subsystems may include an exercise selector 140, a body detector 142, a key points identifier 144, a motion detector 146, a form comparer 148, a range determiner 150, a response provider 152, a form receiver 154, a form storage 156, a silhouette receiver 158, a silhouette recorder 160, a silhouette comparer 162, and a plane analyzer 164. It should be noted that not every system may include every one of these subsystems. A system may only include some of these subsystems, as some subsystems are necessary only for the implementation of features of some systems.

These subsystems interact with image data received from camera 170. In one embodiment, key points on images of the body of user 180 are identified and the motion of the key points. Such an approach is illustrated and explained in greater detail with respect to FIGS. 2A-D. In another embodiment, user motion is analyzed by considering how the silhouette of a user changes over time. Such an approach is illustrated and explained in greater detail with respect to FIG. 3. Each of these approaches is discussed in further detail below, including the steps involved and how the subsystems of application layer 130 provide the functionality of the approach.

Computer system 100 may use network connection 190 to communicate with other processing machines via network 192. Network connection 190 may use an appropriate wired connection or appropriate wireless technology to access network 192. Network 192 may be the Internet, a local area network, or any other network 192 of machines with which computer system 100 may exchange data. It is to be noted that computer system 100 may be connected by network 192 via network connection 190 to server 194 that provides web browser 140 with a source of content as discussed above.

Each of the constituent parts of a system may be implemented on any computer system. Such a computer system can include, but is not limited to, a personal computer, mobile device such as a mobile phone, workstation, embedded system, game console, television, set-top box, or any other computer system. Further, the computer system can include, but is not limited to, a device having a processor and memory for executing and storing instructions. Software may include one or more applications and an operating system. Hardware can include, but is not limited to, a processor, memory and graphical user interface display. The computer system may also have multiple processors and multiple shared or separate memory components. For example, the computer system may be a clustered computing environment or server farm.

Each of the constituent parts of the system may be implemented in hardware, software, firmware, or any combination thereof. Likewise, modules or instructions that constitute operative parts of systems may utilize any type of structured memory, including a persistent memory. In examples, each data storage infrastructure may be implemented as a relational database.

It should be noted that computer-readable medium embodiments may include any physical medium which is capable of having instructions encoded therein that may subsequently be used by a processor to implement methods described herein. Example physical media may include floppy discs, optical discs (e.g. CDs, mini-CDs, DVDs, HD-DVD, Blu-ray), hard drives, punch cards, tape drives, flash memory, and memory chips. However, any other type of tangible, persistent storage that can serve in the role of providing instructions to a processor may be used to store the instructions in the computer-readable medium.

Figure 2A:
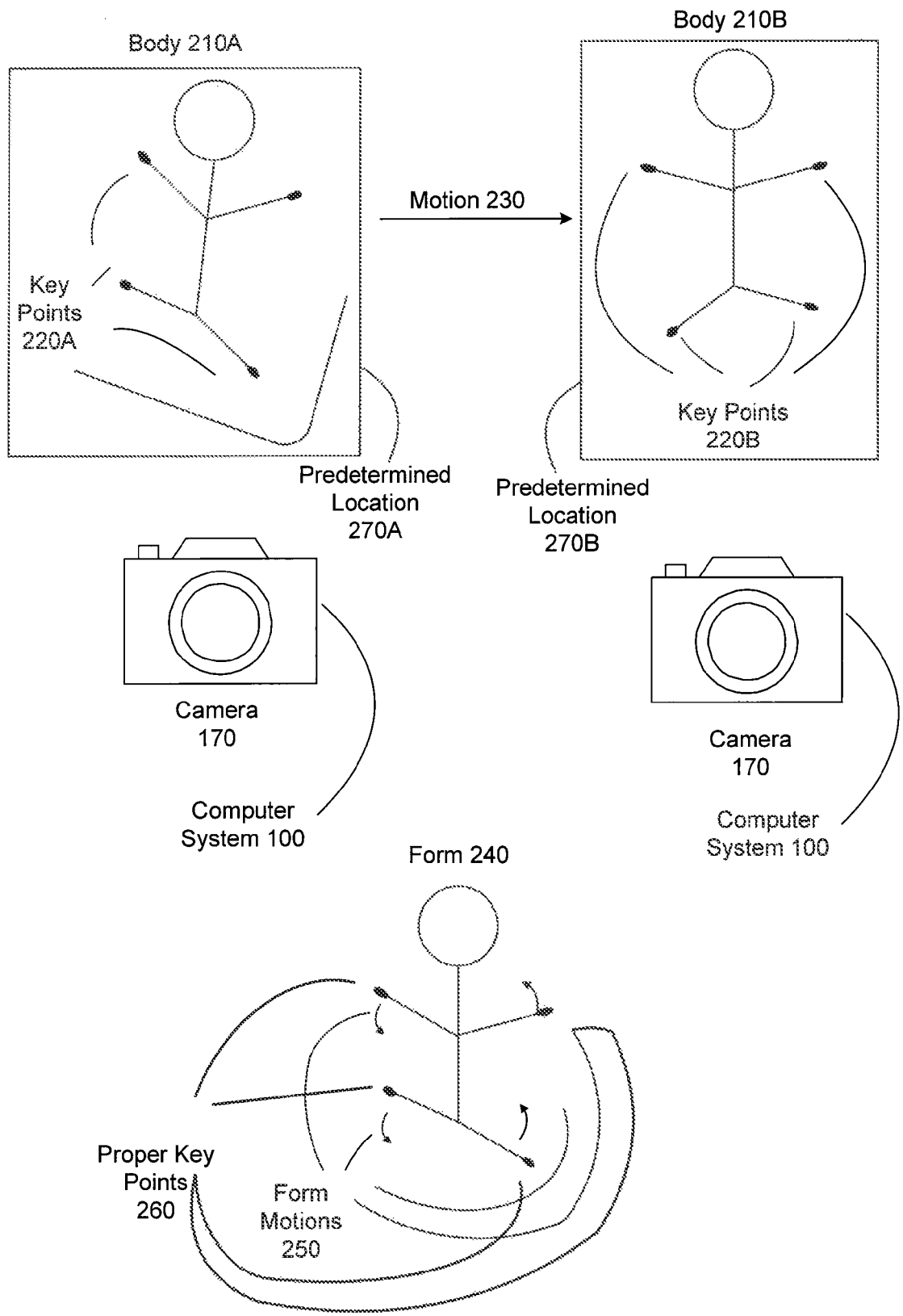
FIG. 2A is a diagram of an example motion of a user and how it is analyzed.
Figure 2B:
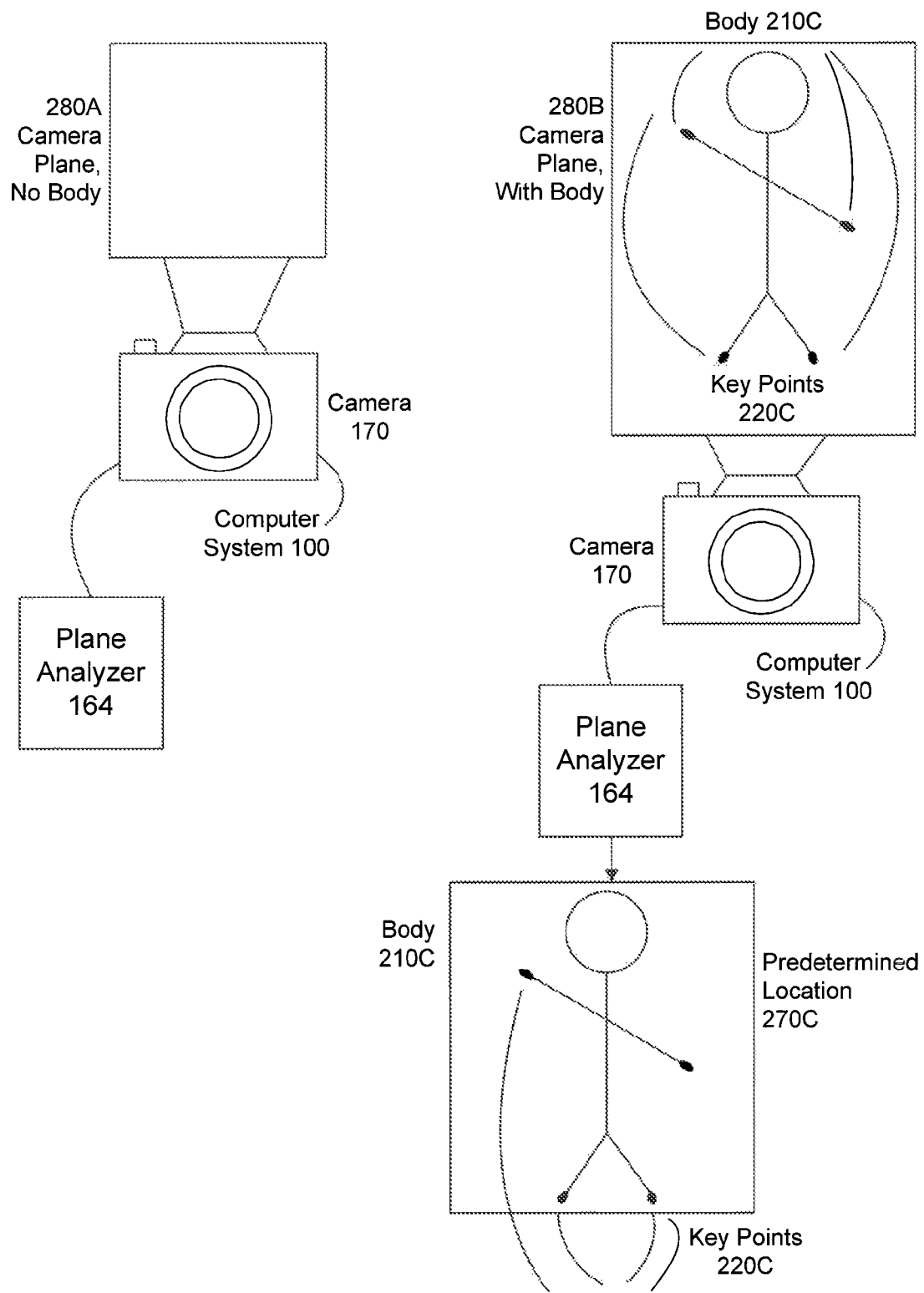
FIG. 2B is another diagram of the motion of a user and how it is analyzed.
Figure 2C:
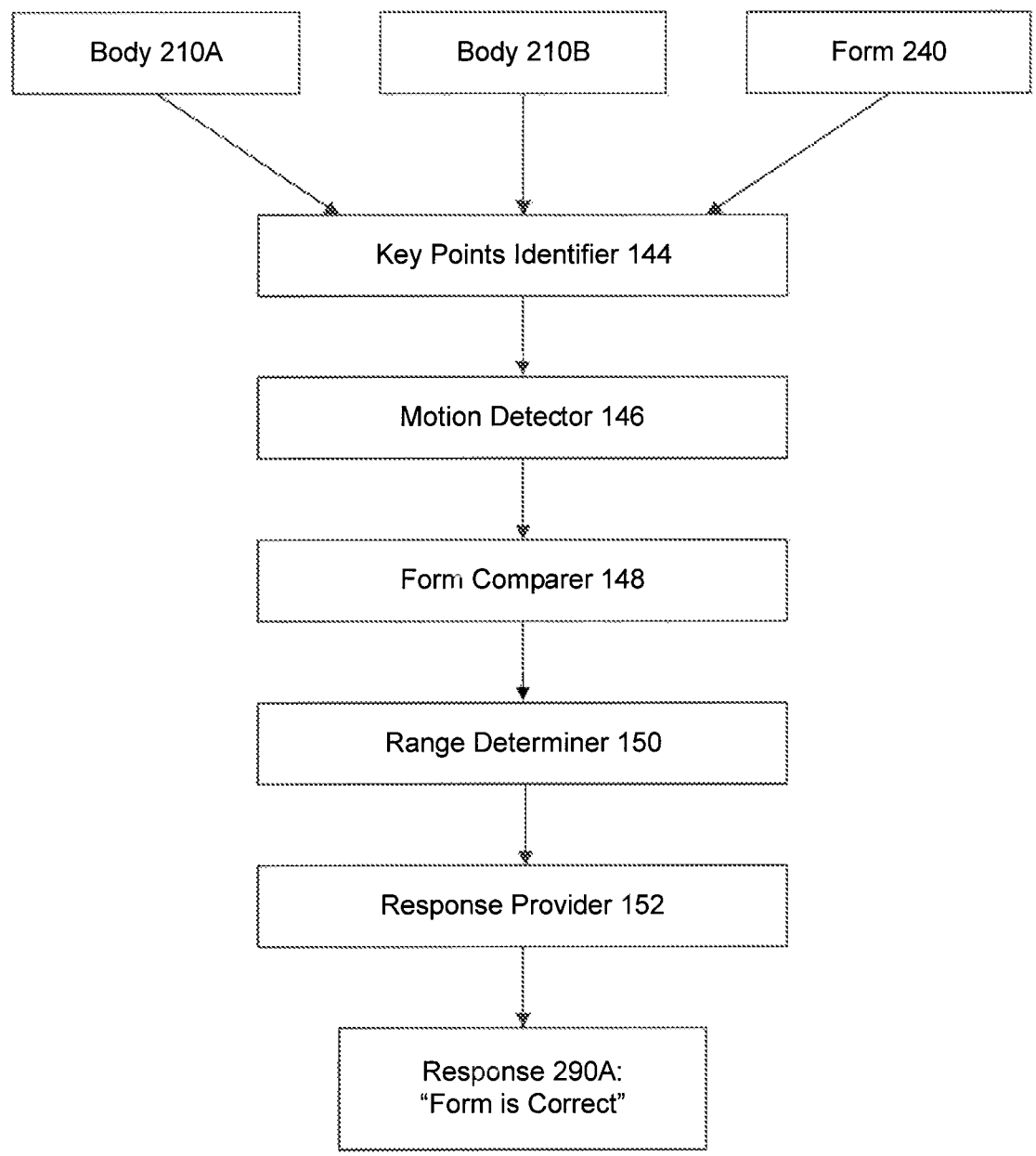
FIG. 2C is a data flow diagram associated with analysis of the motion of a user.
Figure 2D:
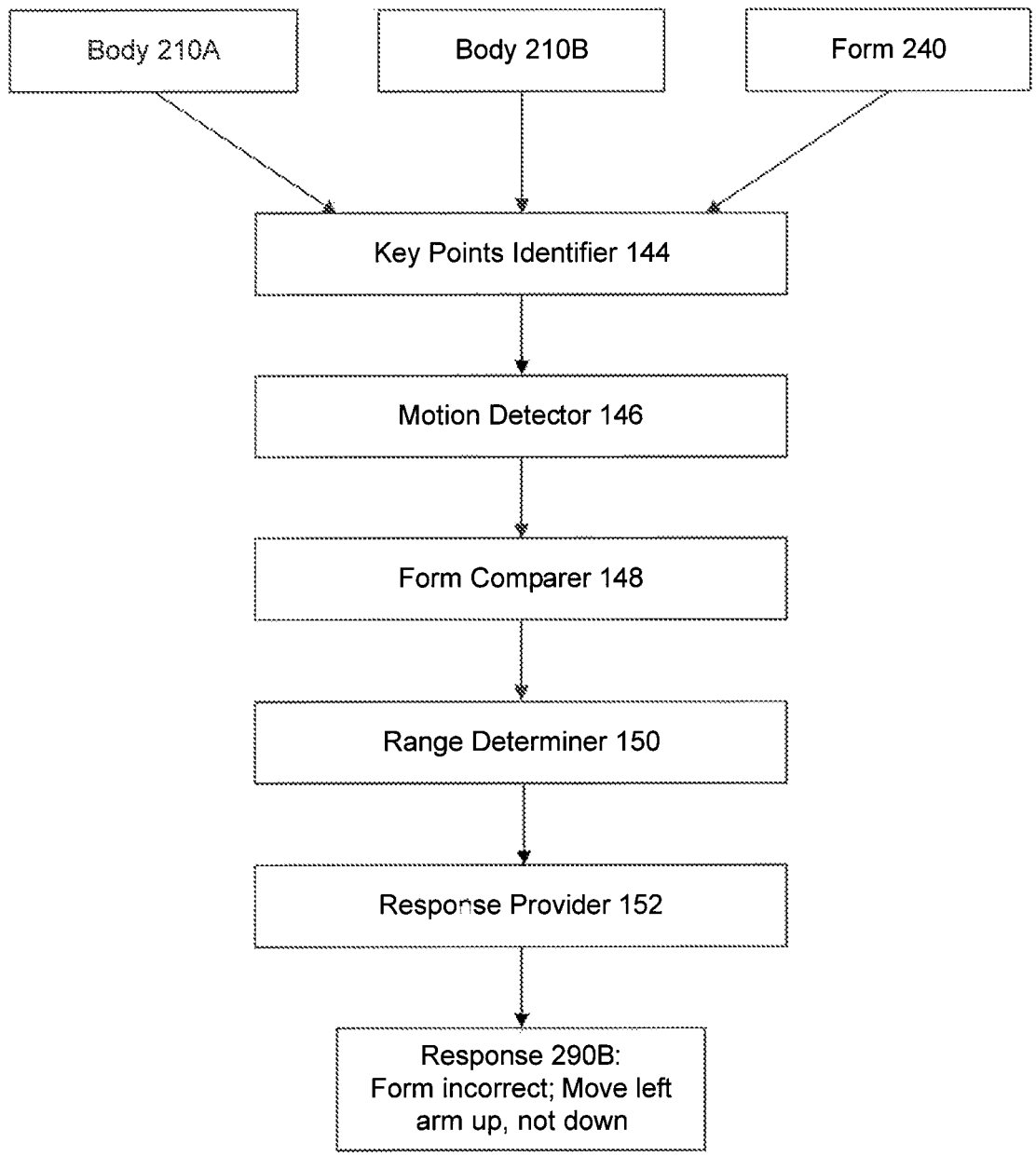
FIG. 2D is another data flow diagram associated with analysis of the motion of a user.

FIGS. 2A-D include diagrams of the motion of the user and how it is analyzed using key points. FIG. 2A is a diagram of an example motion of a user and how it is analyzed. FIG. 2B is another diagram of the motion of a user and how it is analyzed. FIG. 2C is a data flow diagram associated with analysis of the motion of a user. FIG. 2D is another data flow diagram associated with analysis of the motion of a user.

In one embodiment, computer system 100 may be implemented on a tablet hardware platform with a front-facing camera 170. However, as discussed, many types of computer system 100 may obtain image data from camera 170 and use it to track the motion of user 180. Application layer may include information about a set of exercises with proper form information and common mistakes. Such information would be stored in terms of key points and motion of these points on the individual and equipment during execution with acceptable ranges of variation. The information may be stored either as a sequence of positions of the key points that should occur in an ideal execution of the form, a set of positions of the key points at various points in time, an initial set of positions of the key points and their desired trajectories, or another set of information that indicates where the key points may be as user 180 exercises. Additionally, there should be ranges of variation. For example, the locations may be surrounded by an acceptable radius, such that range determiner may judge that key points within the acceptable radius of the stored ideal key point locations may be considered acceptable. The exercise information may be stored in form storage 156.

User 180 can initialize the system by selecting an exercise that he or she wishes to perform. As is discussed below, a wide variety of approaches may provide user 180 with a choice of exercises, and input means may then allow user 180 to choose the exercise. Camera 170 may obtain an image of body 210A and then have key points identifier 144 identify the key points on body 210A by processing the image, such as identifying key points 220A on body 210A. Key points are points obtained from images of a the body of user 180 which, when tracked over time, provide meaningful information about the movement of user 180. However, the specific key points which are identified may vary.

As a simple illustration of how key points are chosen, key points 220A, 220B, 220C and proper key points 260 are located at the end of the limbs of user 180, i.e. at the hands and feet of user 180. However, many more choices of key points are possible. For example, key points may be chosen to provide information about the movement of other joints of user 180, such as the elbow or knee of user 180, or other points associated with known locations on the head or torso of a user 180. For example, key points for a neck roll exercise may include several key points for the head and shoulders of user 180 to establish the characteristics of the motion of the head of user 180 with respect to his or her torso.

Key points may be chosen to capture as many aspects as possible of the motion of user 180. Key points may also be chosen so as to emphasize specific types of user motion, such as moving the right arm of user 180 or rotation to change the orientation of user 180. For example, if the right arm of user 180 is to be tracked, a series of key points may be associated at intervals along the length of the right arm of user 180.

Key points, such as key points 220A, may be obtained by processing an image of the body of user 180, such as body 210A, obtained by camera 170 integrated into computer system 100. Ideally, body 210A may be in a predetermined location 270A, such that body 210A is aligned in a known way with camera 170. Processing the image may be much easier if predetermined location 270A is able to provide body detector 142 and key points identifier 144 with information that guarantees that, for example, user 180 is directly in front of camera 170, a specified distance away (for example, two meters), and is directly facing the camera. Thus, predetermined location 270A specifies a specific place for user 180 to stand, as well as the direction in which user 180 faces.

However, key points identifier 144 may be able to determine key points even if the body 210A is not in predetermined location 270A. This capability is important, especially because the location and position of body 210A may change during an exercise. In order to facilitate using key points identifier 144 to determine key points 220A in the case when body 210A is not in predetermined location 270A, body detector 142 may begin by making an initial guess of where it would expect key points 220A to be, and then progressively transform the set of key points 220A to reflect where key points 220A actually are based on the location and orientation of 210A.

Other techniques may recognize key points as user 180 moves and turns with respect to camera 170. As discussed below, body detector 142 may also need to proceed based on information about the size of user 180. For example, body detector 142 may need information about the height and body shape of user 180, as body detector 142 needs to be able to distinguish between a user that is 2 meters tall and 3 meters from camera 170, versus a user that is 1.6 meters tall and 2.5 meters from camera 170. Such a distinction may proceed based on information provided by user 180, or feature detection of the images provided by camera 170 to deduce the height of user 180. Additionally, if multiple cameras are used, depth information may be available that can help to ascertain the size of user 180.

A variety of techniques may be used to deduce key points. For example, image processing techniques such as edge detection algorithms may deduce an outline of body 210A by looking for clues from the image of body 210A such as abrupt color changes. Another technique is to use templates with expected positions of key points 220A, and to transform the expected positions of key points 220A to reflect translations, rotations, and the like of body 210A, until the key points 220A provided by the template correspond with the image. Further image processing may divide the image of body 210A into regions, such as left and right arm, left and right leg, torso, and head. Additionally, various cues from the image may allow identification of information such as the direction user 180 is facing and how far away user 180 is. For example, image processing may analyze the head of user 180 to characterize the direction user 180 is facing by taking into account whether camera 170 sees a rear view of the head of user 180 (i.e., hair or a bald spot), a frontal view of the head of user 180 (i.e., a face), or a profile. Also, user 180 may provide an embodiment with information it can use to aid in deducing key points. For example, if user 180 provides height information, that information can be used in conjunction with information from camera 170 to guess the distance of user 180.

Once the image processing establishes the position and orientation of user 180 and divides the image into regions, heuristics and feature detection algorithms can provide information to help determine where the key points are. For example, image processing may determine the location of a hand and an elbow by processing an arm region of an image. The hand may be identified as the terminus of the arm region, while the elbow may be identified as the approximate middle of the arm region, or may be identified by feature detection to identify a bend in the arm region. Alternatively, the feature detection may identify multiple points to help identify motion. For example, a number of key points may be identified along the torso of user 180 to track the torso of user 180 as user 180 performs toe touches.

User 180 may then perform an exercise, preferably in a known location, such as predetermined location 270A, in front of computer system 100. As the exercise is being performed the system may track the key points and determine how close user 180 is to following the proper form. For example, camera 170 may take a picture of body 210A at one time, a picture of body 210B at another time, and so on. Camera 170 may be configured to take a series of pictures at regular time intervals, or it may attempt to take pictures at specific stages of a given exercise. For example, if user 180 is doing jumping jacks, camera 170 may attempt to take pictures when the arms and legs of user 180 are together, when they are further apart, and at two places in between. Camera 170 may be a video camera that takes a series of pictures at a set rate of frames-per-second (FPS). For each picture, image processing occurs as discussed above to associate key points with the picture. For example, the images associated with body 210A and body 210B provide key points 220A and key points 220B respectively. For simplicity, both body 210A and body 210B are associated with predetermined locations 270A and 270B, such that user 180 is located in front of camera 170 at a specified distance, facing camera 170 directly. Between body 210A and body 210B, user 180 has moved his or her left arm and leg up, and right arm and leg down. Motion detector 146 compares images, using key points identifier 144 to find the key points at each image and determines the translation involved in moving the key points from image to image. Motion detector 146 may consider motion 230 of groups of key points at once to capture the motion of part of body 210A of user 180. For example, if multiple key points are tracked along the right leg of user 180, motion detector 146 may analyze the key points as a group so as to characterize the motion of right leg of user 180 as a unit.

Form comparer 148 works with motion detector 146 to compare the actual motion of user 180 to an ideal motion. The system has access to form data, such as form 240. The information may be stored in form storage 156. Form 240 may include information about form motions 250, as defined with respect to proper key points 260. For example, form motions 250 define moving the right limbs of user 180 down slightly, and the left limbs of user 180 up slightly. Form motions 250, in general, may define how the position of the proper key points 260 should change over time. Such position changes may include vector information, including direction and magnitude of the motion of each of proper key points 260. It should be noted that the form motion 250 may need to be scaled or adapted to reflect issues such as the size and position of user 180. For example, form motions 250 should be able to automatically adjust if a user 180 is short or tall, overweight or underweight, or in various positions with respect to camera 170. Such a result may be obtained by using various transformation on the vectors of the position changes, such as scaling, rotation, and translations, so that form motions 250 are relevant in a wide variety of use cases. Part of using form motions 250 is that they define a range of motion. Motion detector 146 can capture motion 230, and form comparer 148 can compare motion 230 to form 240, with range determiner 150 ascertaining that motion 230 falls within a set range of motion. For example, form motions 250 may define moving the left arm of user 180 down by a range of 10-20 degrees, with an ideal of 15 degrees down. Range determiner 150 works with form comparer 148 to establish whether user 180 is within range.

For example, motion detector 146 may identify that the right hand of user 180 has moved up by 8 inches. Form comparer 148 may determine that the ideal motion is a movement up of 7 inches. Range determiner 150 may establish that a range of 6-9 inches up is acceptable, so range determiner may establish that the motion of the key point associated with the right hand of user 180 is correct.

If user 180 is starting to drift out of the acceptable range the system may determine which of the common mistake forms that user 180 is actually in. This determination may be made by cooperation between form comparer 148 and range determiner 150. For example, if user 180 moved his or her right hand up by 10 inches, form comparer 148 and range determiner 150 can establish that the right hand was moved up too far. Likewise, if user 180 moved his or her right hand up by 4 inches, form comparer 148 and range determiner 150 can establish that the right hand was not moved up far enough. In order for motion 230 of a key point to be correct, both the direction and magnitude of motion need to be correct. As discussed, correct motion can be verified by establishing a destination for a key point and establishing an acceptable radius. The system may then prompt user 180 with a script response indicating what user 180 is doing that is incorrect and how to correct the motion of user 180. The prompting may be performed by response provider 152.

Further aspects of the operation of an embodiment that uses key points are illustrated in FIGS. 2B-D, which are now described. Computer system 100 uses camera 170 to capture images of body 210A and body 210B, which represent images of user 180 at different points in time. As discussed above, by using various image processing techniques, computer system analyzes the images of body 210A and body 210B to result in key points 220A for body 210A and key points 220B for body 210B. For example the analysis may be carried out by body detector 142 and key points identifier 144. The key points may be identified as corresponding with the hands and feet of user 180. Body detector 142 and key points identifier establish the positions of key points 220A and 220B at various points in time.

For example, the image processing required to identify key points may use a technique depicted in FIG. 2B. In FIG. 2B, camera 170 takes a picture of camera plane 280A, without the body of user 180 being present, and a picture of camera plane 280B, with body 210C being present. These pictures are then sent to a plane analyzer 164 for analysis 164. By comparing the pictures with and without body 210C, plane analyzer 164 can establish the edges of body 210C by identifying edges based on pixel changes. Plane analyzer identifies changes between pictures with and without body 210C. Plane analyzer 164 can determine where body 210C is, where it was not before. Also at this time, identification of key points 220C can proceed as discussed above. Plane analyzer 164 can then establish a predetermined location 270C associated with body 210C and key points 220C. Thereafter, it may be easier for key points identifier 144 and motion detector 146 to track user 180 based on predetermined location 270C established by plane analyzer 146.

In one embodiment, training can be used. For example, the system may take pictures of user 180 at specified locations and specific postures. By so doing, the system may use variety of machine learning techniques that facilitate proper determination of key points. For example, the system may use supervised learning to associate specific image data with specific user positioning. By providing a system that is trained, it may be easier for the subsystems of the system to determine positions of key points. It may be noted that training, may also be used in the context of a silhouette embodiment, as discussed below with respect to FIG. 3. Since training may provide information about what an image of a given user position should look like, training may service as a basis for comparison when identifying the key points. For example, training may take an image of user 180 in a series of known positions. When key points identifier 144 attempts to determine key points, it can ascertain which of the known positions is closes to the obtained position and use this information as a starting point to help establish where the key points associated with the image should be placed.

In the example provided in FIG. 2A, this key point comparison should indicate that motion 230 of user 180 is correct from body 210A to body 210B. Given that user 180 faces the camera, user 180 moves his or her right hand and foot down, and his or her left and foot up, corresponding with form 240. However, if user 180 deviates from the form, by moving key points the wrong direction or distance, computer system 100 may identify this discrepancy and provide user 180 with suggestions by response provider 152, as provided above.

However, if one compares body 210A to body 210C, the exercise may be incorrect and feedback may be provided. In this case, user 180 has moved his or her left arm down, not up as desired.

For example, FIG. 2C provides images of body 210A, body 210B, and form 240. These images are processed by key points identifier 144, motion detector 146, form comparer 148, range determiner 150, and response provider 152 in sequence as discussed above. The result is response 290A, "Form is correct", because user 180 has moved his or her limbs properly.

By contrast, FIG. 2D provides images of body 210A, body 210C, and form 240. These images are processed by key points identifier 144, motion detector 146, form comparer 148, range determiner 150, and response provider 152 in sequence as discussed above. The result is response 290B, "Form is incorrect: Move left arm up, not down", because user 180 has moved most of his or her limbs properly, but moved the left arm in the wrong direction. As noted, motion 230 of user 180 is only correct if the direction and magnitude of the movement of the key points is correct; as transformed to reflect the position, orientation, and size of user 180.

Figure 3:
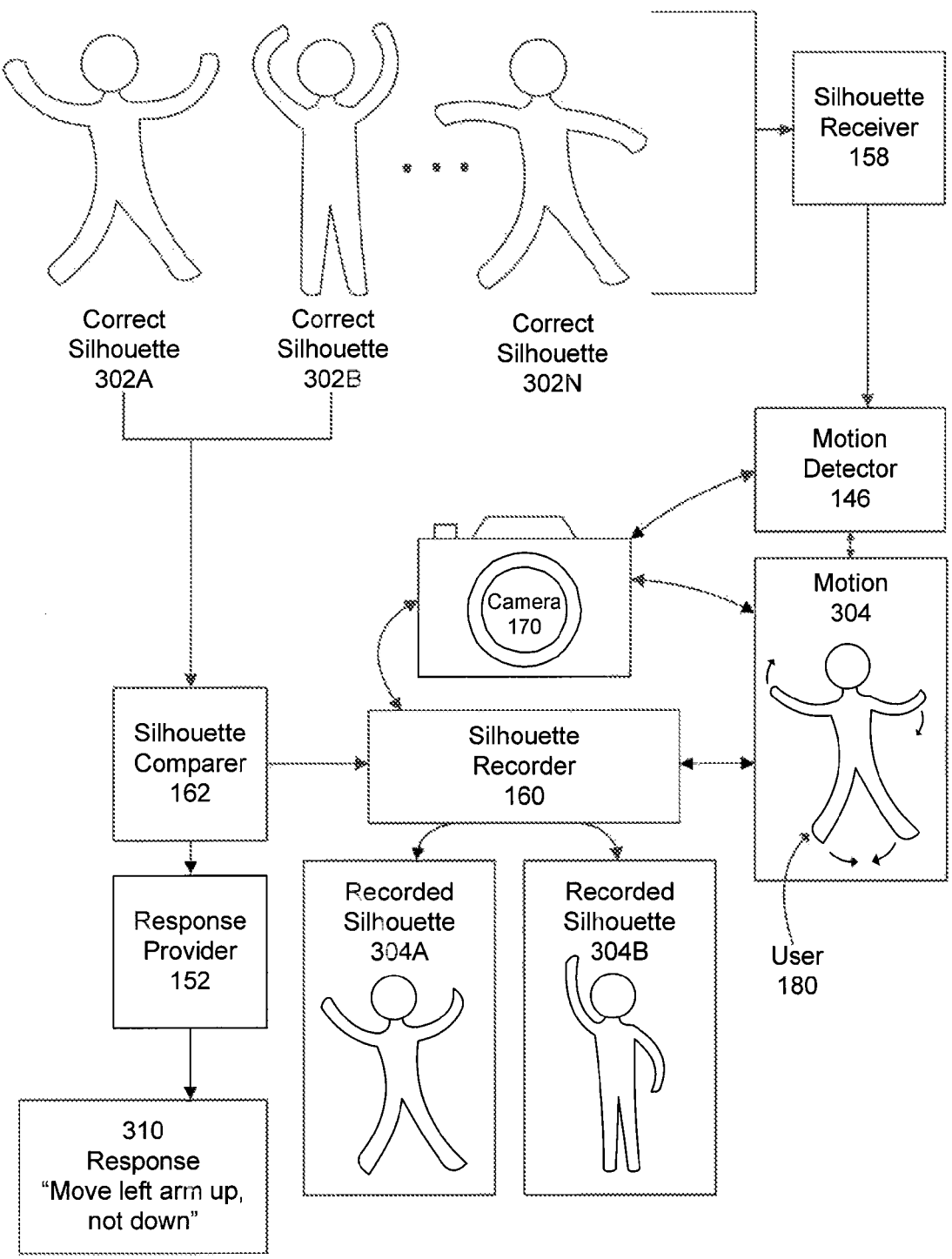
FIG. 3 is a diagram of an example motion of a user and how it is analyzed.

FIG. 3 is a diagram of an example motion of a user and how it is analyzed. Silhouette receiver 158 receives a series of correct silhouettes 302A, 302B ... 302N. The silhouettes may be retrieved from form storage 156. A silhouette is processed as an outline. For example, a silhouette may be a vector image or a bitmapped image. The silhouettes represent two-dimensional outlines of user 180 involved in a series of motions. Camera 170 tracks the motion of user 180 in conjunction with motion detector 146. Camera 170 uses silhouette recorder 160 to record multiple recorded silhouettes such as 304A and 304B, as user 180 moves over time. Recording silhouettes operates by capturing an image of user 180 using camera 170, using edge detection to establish the boundaries of the silhouette, and storing the outline of the silhouette. Motion detector 146 detects motion by comparing recorded silhouettes such as 304A and 304B. For example, motion 304 includes a silhouette lifting its right arm, lowering its left arm, and drawing its legs together. Silhouette comparer 162 compares correct silhouettes 302A, 302B ... 302N to recorded silhouettes such as 304A and 304B. In general, the comparison may proceed by subdividing the silhouettes into regions and identifying transformations associated with the motion of each region, and then providing a response based on the transformations. For example, the feedback may include a response indicating if the motion associated with the user is correct. If the motion associated with the user is not correct, the feedback may additionally include a response indicating how to correct the motion of the user. An appropriate response is thus provided to user 180 by response provider 152, such as response 310, "Move left arm up, not down".

Figure 4:
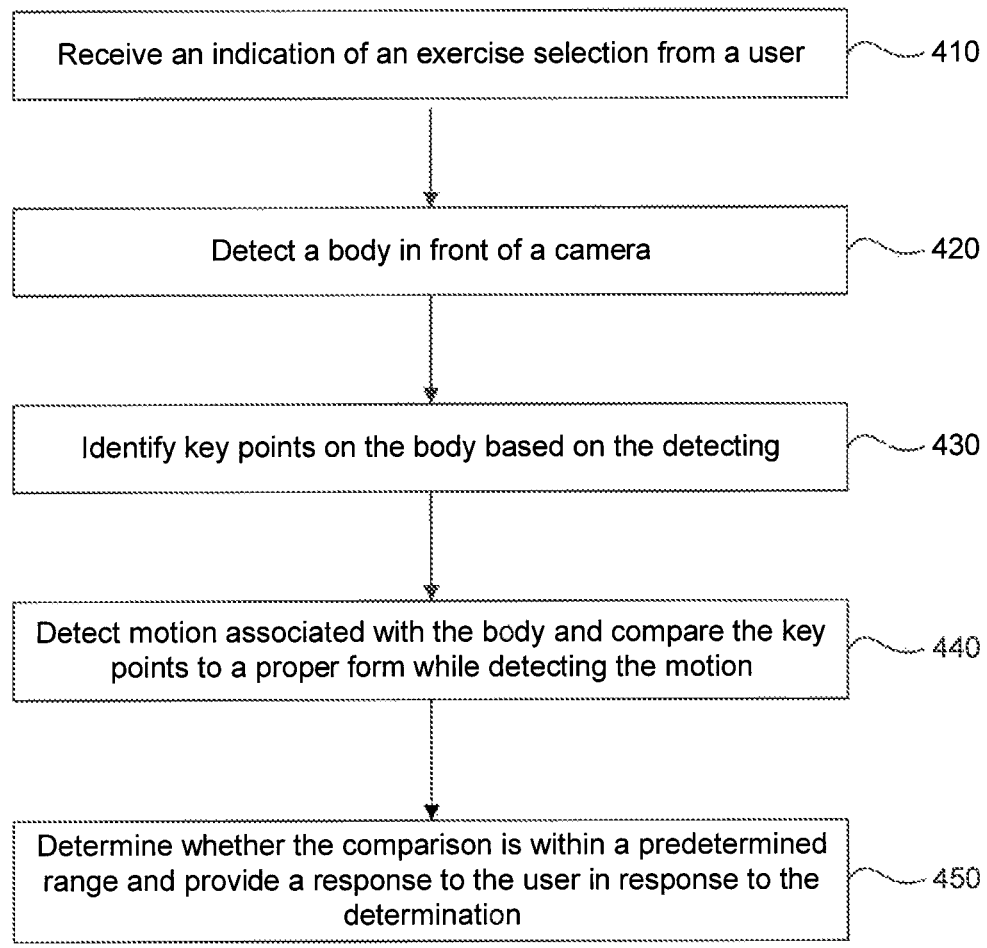
FIG. 4 is a flowchart of an exemplary method for providing feedback for a user involved in exercise.

FIG. 4 is a flowchart of an exemplary method for providing feedback for a user involved in exercise.

In stage 410, an indication is received of an exercise selection from a user. For example, stage 410 may be performed by exercise selector 140 based on input from user 180. In general, exercise selector 140 may receive input from user 180 that determines a choice of exercise. For example, exercise selector 140 may display, using an output means, a selection of exercises, such as push-ups, neck rolls, jumping jacks, etc. User 180 may then provide input to select an exercise, using an input means. For example, a graphical display may provide a list of exercises, which user 180 may pick from using an input device such as a keyboard, mouse, or infrared or BLUETOOTH remote control. Alternatively, an input device may be configured to pick an exercise directly, without prompting. For example, an input device may have a switch which may be set to different exercise types, which chooses that exercise when a button is pushed. It may be recognized that a wide variety of output and input means may be used to obtain the exercise selection, and the precise method of selection may vary.

In stage 420, a body is detected in front of a camera. For example, stage 420 may be performed by body detector 142, using information from camera 170. As discussed above with respect to FIG. 2B, plane analyzer 164 may use information from camera 170 based on camera plane 280A with no body in comparison to camera plane 280B with a body. However, body detector 142, as discussed above, may use image processing techniques to establish that a body such as body 210A is present in front of camera 170. For example, edge and feature detection techniques may isolate edges and regions with appropriate shapes and colorations that may identify that a body is present in front of camera 170. In order to facilitate detecting body 210A of user 180, camera 170 may periodically take pictures of its environment, and use body detector 142 to establish whether user 180 has moved into position to begin exercising.

In stage 430, key points are identified on the body based on the detecting. For example, stage 430 may be performed by key points identifier 144. As discussed above, body detector 142 obtains an image of a body, such as body 210A, and then key points identifier 144 processes the image using various techniques such as feature detection and edge detection to identify key points 220A for body 210A. For example, feature detection may place key points at the hands and feet of user 180, as provided in an example. Also as discussed above, training may be used to provide example images associated with specific user locations and postures that may help identify the location of the key points.

In stage 440, motion is detected associated with the body and the key points are compared to a proper form while detecting the motion. For example, stage 440 may be performed by motion detector 146 and form comparer 148 by accessing form storage 156. Motion detection and comparing the key points to the form are discussed above. In general, these stages detect either a series of positions of key points at different times, and/or positions of key points and their trajectories. These stages involve establishing such motion information about the actual key points, and comparing the motion with proper key points 260 to establish the difference in position between actual key points and proper key points. The comparison may be performed at predefined time intervals. Alternatively, the comparison may be performed at specific stages of the exercise.

In stage 450, it is determined whether the comparison is within a predetermined range and a response is provided to the user in response to the determination. For example, stage 450 may be performed by range determiner 150 and response provider 152. Establishing a range, as discussed above, proceeds by finding an appropriate range of motion for each key point, based on data from form storage 156, and analyzing the motion of the key point to establish if it falls into the range of motion. For example, the response may indicate whether or not user 180 is following the proper form. Additionally, when user 180 is not following the proper form, the response may indicate how to correct the motion of user 180.

Figure 5:
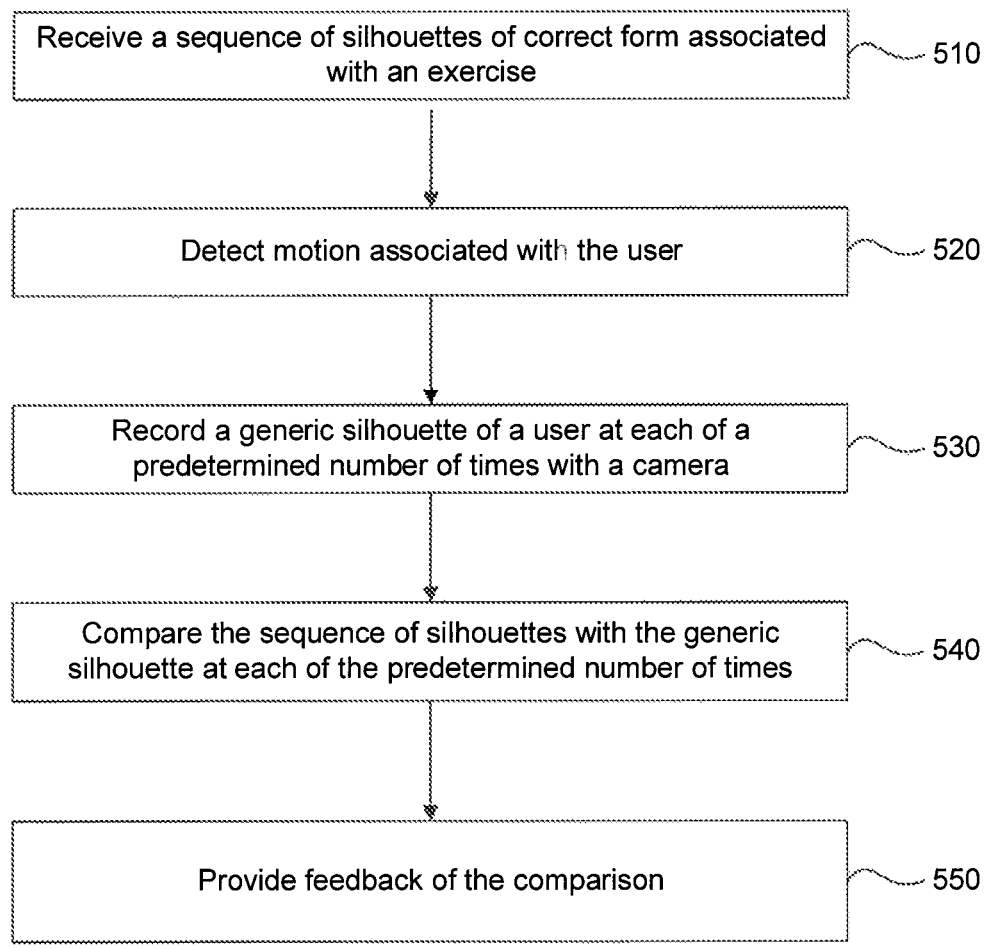
FIG. 5 is a flowchart of another exemplary method for providing feedback for a user involved in exercise.

FIG. 5 is a flowchart of another exemplary method for providing feedback for a user involved in exercise.

In stage 510, a sequence of silhouettes of correct form associated with an exercise are received. For example, stage 510 may be performed by silhouette receiver 158. As discussed above, silhouette receiver retrieves the silhouettes as graphics representing an outline of a user, from form storage 156.

In stage 520, motion associated with the user is detected. For example, stage 520 may be performed by motion detector 146. As discussed above, motion detector 146 may divide the silhouettes into regions, and determine how each of the regions of the silhouettes changes from silhouette to silhouette. For example, motion detector may experiment with various transformations on each region of the silhouettes so as to reflect the movement of user 180.

In stage 530, a generic silhouette of a user at each of a predetermined number of times with a camera is recorded. For example, stage 530 may be performed by silhouette recorder 160. As discussed, camera 170 may record images of user 180 for silhouette recorder 160, and silhouette recorder 160 may establish an outline of each silhouette using techniques such as edge detection. For example, silhouette recorder may record recorded silhouettes 304A and 304B.

In stage 540, the sequence of silhouettes is compared with the generic silhouette at each of the predetermined number of times. For example, stage 540 may be performed by silhouette comparer 162. As discussed above, the recorded silhouettes 304A and 304B may be compared to corresponding correct silhouettes 302A and 302B.

In stage 550, feedback of the comparison is provided. For example, stage 550 may be performed by response provider 152. Providing the feedback involves confirming that the exercise is correct if this is the case, or otherwise specifying what user 180 needs to do differently. Specific examples of this capability have been provided.

As discussed, various embodiments offer a new approach to ensuring that a user is exercising correctly. Rather than relying on observation by the user or an instructor, certain embodiments capture image information and analyze the image information to track the position of the user as it changes over time. The analysis yields information that represents the movement of the user. For example, analysis may reveal how key points on the body of a user or the silhouette of a user changes over time. User motion may be tracked to easily and automatically identify the overall position of the body of the user as well as the movements of parts of the user, such as extremities or head and neck.

By monitoring user execution of exercises, the system may provide several pieces of potentially useful information. If the motion of the user is correct, the system may verify it and the user may know that he or she is exercising correctly. If the motion of the user is incorrect, the system may alert the user. Corrective suggestions may additionally be provided to the user.

Thus, helping to ensure that a user is exercising properly may ensure that a user is exercising in a manner that is both safe and effective.

The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method, comprising:
   receiving an indication of an exercise selection from a user;
   detecting a body in front of a camera;
   determining expected key points on the body based on the detecting;
   establishing a location and an orientation of the body based on height information and image processing;
   identifying key points on the body by transforming the expected key points based on the location and the orientation of the body;
   taking a picture of the body at a stage of an exercise associated with the exercise selection;
   detecting motions of the key points on the body;
   comparing the motions of the key points to a proper form while detecting the motion, the proper form comprising proper key points on an individual and motions of the proper key points; and
   determining whether the comparison is within a predetermined range and providing a response to the user in response to the determination.

2. The method of claim 1, wherein the proper form includes initial positions of the proper key points, and the motions of the proper key points comprise desired trajectories of the proper key points.

3. The method of claim 1, wherein detecting a body in front of a camera further comprises:
   detecting whether the body is standing in a predetermined location in front of the camera.

4. The method of claim 3, further comprising:
   recording a plane of the camera without the body in front of the camera;
   recording the plane with the body present in front of the camera; and
   determining the predetermined location based on the recording of the plane without the body and the recording of the plane with the body.

5. The method of claim 1, further comprising:
   receiving one or more proper forms associated with each of a plurality of exercises.

6. The method of claim 1, wherein providing a response to the user in response to the determination further comprises:
   providing a response indicating whether or not the user is following the proper form.

7. The method of claim 6, wherein providing a response to the user in response to the determination further comprises:
   when the user is not following the proper form, providing a response indicating how to correct the motion of the user.

8. A system, comprising:
   one or more processors; and
   a non-transitory machine-readable medium comprising instructions stored therein, which when executed by the processors, cause the processors to perform operations comprising:
      receiving an indication of an exercise selection from a user;
      detecting a body in front of a camera;
      determining expected key points on the body based on the detecting;
      determining a distance of the body based on height information;
      determining a location and an orientation of the body based on the distance and image processing;
      identifying key points on the body by transforming the expected key points based on the location and the orientation of the body;

taking a picture of the body at a stage of an exercise associated with the exercise selection;

detecting motions of the key points on the body;

comparing the motions of the key points to a proper form while detecting the motion, the proper form comprising proper key points on an individual and motions of the proper key points;

determining whether the comparison is within a predetermined range; and providing a response to the user in response to the determination.

9. The system of claim 8, wherein the proper form includes initial positions of the proper key points, and the motions of the proper key points comprise desired trajectories of the proper key points.

10. The system of claim 8, wherein the detecting a body in front of a camera further comprises:

detecting whether the body is standing in a predetermined location in front of the camera.

11. The system of claim 10, wherein the operations further comprise:

recording a plane of the camera without the body in front of the camera;

recording the plane with the body present in front of the camera; and determining the predetermined location based on the recording of the plane without the body and the recording of the plane with the body.

12. The system of claim 8, wherein the operations further comprise:

receiving one or more proper forms associated with each of a plurality of exercises.

13. The system of claim 8, wherein the providing a response to the user in response to the determination further comprises:

providing a response indicating whether or not the user is following the proper form.

14. The system of claim 13, wherein the providing a response to the user in response to the determination further comprises:

when the user is not following the proper form, providing a response indicating how to correct the motion of the user.

15. A non-transitory computer readable storage medium having instructions stored thereon that, when executed by one or more processors, cause the one or more processors to execute a method, the method comprising:

receiving an indication of an exercise selection from a user;

detecting a body in front of a camera;

determining expected key points on the body based on the detecting;

determining a distance of the body based on height information;

determining a location and an orientation of the body based on the distance and image processing;

identifying key points on the body by transforming the expected key points based on the location and the orientation of the body;

taking a picture of the body at a stage of an exercise associated with the exercise selection;

detecting motions of the key points on the body based on the picture;

comparing the motions of the key points to a proper form while detecting the motion, the proper form comprising proper key points on an individual and motions of the proper key points; and determining whether the comparison is within a predetermined range and providing a response to the user in response to the determination.

16. A computer-implemented method comprising:

receiving a sequence of silhouettes of correct form associated with an exercise;

detecting motion associated with the user;

recording a generic silhouette of the user at each of a predetermined number of times with a camera based on detecting specific stages of the exercise;

comparing the sequence of silhouettes with the generic silhouette at each of the predetermined number of times by subdividing each of the sequence of silhouettes and each of the generic silhouettes into regions and identifying a transformation associated with a motion of each region; and providing feedback of the comparison.

17. The method of claim 16, wherein the feedback comprises a response indicating if the motion associated with the user is correct.

18. The method of claim 17, wherein if the motion associated with the user is not correct, the feedback additionally comprises a response indicating how to correct the motion of the user.

* * * * *